United States Patent
Murphy et al.

(10) Patent No.: US 12,186,498 B2
(45) Date of Patent: *Jan. 7, 2025

(54) ROBOTIC CATHETER SYSTEM WITH VARIABLE SPEED CONTROL

(71) Applicant: Corindus, Inc., Waltham, MA (US)

(72) Inventors: John Murphy, North Reading, MA (US); Tal Wenderow, Newton, MA (US); David Handler, Newton, MA (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 219 days.

This patent is subject to a terminal disclaimer.

(21) Appl. No.: 17/457,093

(22) Filed: Dec. 1, 2021

(65) Prior Publication Data
US 2022/0088349 A1    Mar. 24, 2022

Related U.S. Application Data

(63) Continuation of application No. 15/680,999, filed on Aug. 18, 2017, now Pat. No. 11,213,654, which is a
(Continued)

(51) Int. Cl.
*A61M 25/01* (2006.01)
*A61B 34/30* (2016.01)
(Continued)

(52) U.S. Cl.
CPC .......... *A61M 25/0105* (2013.01); *A61B 34/30* (2016.02); *A61B 2017/00243* (2013.01);
(Continued)

(58) Field of Classification Search
CPC .......... A61M 25/0105; A61M 25/0113; A61B 34/30; A61B 2017/00243; A61B 2034/301; A61B 2090/376
See application file for complete search history.

(56) References Cited

U.S. PATENT DOCUMENTS 5,492,131 A    2/1996  Galel
6,083,170 A    7/2000  Ben-Haim
(Continued)

OTHER PUBLICATIONS

International Searching Authority, Written Opinion of the International Searching Authority for Application No. PCT/US2011/026449, May 26, 2011, 6 pages.
(Continued)

*Primary Examiner* — Richard G Louis

(57) ABSTRACT

A robotic catheter procedure system includes a bedside system that has a percutaneous device, and an actuating mechanism configured to engage and to impart movement to the percutaneous device. The system also includes a workstation coupled to the bedside system. The workstation includes a user interface configured to receive a user input, ma display device configured to display an image, a control system operatively coupled to the user interface and the actuating mechanism. The control system is configured to generate a control signal and the actuating mechanism causes movement of the percutaneous device in response to the control signal. The control system is configured to slow movement of the percutaneous device via the actuating mechanism as an identified point on the percutaneous device approaches a structure requiring a change in direction of the percutaneous device.

14 Claims, 6 Drawing Sheets

Related U.S. Application Data continuation of application No. 13/600,824, filed on Aug. 31, 2012, now Pat. No. 9,764,114, which is a continuation of application No. PCT/US2011/026449, filed on Feb. 28, 2011.

(60) Provisional application No. 61/309,764, filed on Mar. 2, 2010.

(51) Int. Cl.
    *A61B 17/00* (2006.01)
    *A61B 90/00* (2016.01)

(52) U.S. Cl.
    CPC ... *A61B 2034/301* (2016.02); *A61B 2090/376* (2016.02); *A61M 25/0113* (2013.01)

(56) References Cited

U.S. PATENT DOCUMENTS

| | | | |
|---|---|---|---|
| 6,119,033 A * | 9/2000 | Spigelman | A61B 90/36 600/426 |
| 2001/0025142 A1 | 9/2001 | Wessels et al. | |
| 2002/0016564 A1 * | 2/2002 | Courtney | A61B 17/22 606/200 |
| 2002/0193873 A1 | 12/2002 | Brucker et al. | |
| 2004/0044279 A1 | 3/2004 | Lewin et al. | |
| 2005/0065435 A1 * | 3/2005 | Rauch | A61B 34/73 600/427 |
| 2005/0197557 A1 * | 9/2005 | Strommer | A61B 5/06 600/407 |
| 2006/0041181 A1 | 2/2006 | Viswanathan et al. | |
| 2006/0074297 A1 | 4/2006 | Viswanathan | |
| 2008/0108873 A1 | 5/2008 | Gattani et al. | |
| 2008/0287783 A1 | 11/2008 | Anderson | |
| 2009/0105639 A1 | 4/2009 | Weitzner et al. | |
| 2009/0137952 A1 | 5/2009 | Ramamurthy et al. | |
| 2009/0221958 A1 | 9/2009 | Beyar et al. | |
| 2012/0158011 A1 * | 6/2012 | Sandhu | A61B 34/30 606/130 |

OTHER PUBLICATIONS

EESR for EP Application 19162394.1; mail date Sep. 12, 2019; 9 pages.

* cited by examiner

ROBOTIC CATHETER SYSTEM WITH VARIABLE SPEED CONTROL

CROSS-REFERENCE TO RELATED PATENT APPLICATION

This application is a continuation of U.S. application Ser. No. 15/680,999, filed Aug. 18, 2017, which is a continuation of U.S. application Ser. No. 13/600,824, filed Aug. 31, 2012, which is a continuation of international Application No. PCT/US 11/26449, filed Feb. 28, 2011, which claims the benefit of U.S. Provisional Application No. 61/309,764, filed Mar. 2, 2010, which is incorporated herein by reference in its entirety.

BACKGROUND OF THE INVENTION

The present invention relates generally to the field of catheter systems for performing diagnostic and/or intervention procedures. The present invention relates specifically to catheter systems including providing variable speed control for a percutaneous device.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than surgery. If a patient shows symptoms indicative of cardiovascular disease, an image of the patient's heart may be taken to aid in the diagnosis of the patient's disease and to determine an appropriate course of treatment. For certain disease types, such as atherosclerosis, the image of the patient's heart may show a lesion that is blocking one or more coronary arteries. Following the diagnostic procedure, the patient may undergo a catheter based intervention procedure. During one type of intervention procedure, a catheter is inserted into the patient's femoral artery and moved through the patient's arterial system until the catheter reaches the site of the lesion. In some procedures, the catheter is equipped with a balloon or a stent that when deployed at the site of a lesion allows for increased blood flow through the portion of the coronary artery that is affected by the lesion. In addition to cardiovascular disease, other diseases (e.g., hypertension, etc.) may be treated using catheterization procedures.

SUMMARY OF THE INVENTION

In accordance with an embodiment, a robotic catheter procedure system includes a bedside system, the bedside system having a percutaneous device and an actuating mechanism configured to engage and to impart movement to the percutaneous device. The system also includes a remote workstation coupled to the bedside system, the remote workstation having a user interface configured to receive a user input, a display device configured to display an image, and a control system operatively coupled to the user interface and the actuating mechanism, the control system configured to generate a control signal, wherein the actuating mechanism causes movement of the percutaneous device in response to the control signal, wherein the control system is configured to slow movement of the percutaneous device via the actuating mechanism as an identified point on the percutaneous device approaches a structure requiring a change in direction of the percutaneous device.

In accordance with another embodiment, a workstation configured for operating a robotic catheter system having an actuating mechanism configured to engage and to impart movement to a percutaneous device, the workstation including a user interface configured to receive a user input, a display device configured to display an image, and a control system operatively coupled to the user interface, the control system configured to generate a control signal, wherein the actuating mechanism causes movement of the catheter device in response to the control signal, wherein the control system is configured to slow movement of the percutaneous device via the actuating mechanism as an identified point on the percutaneous device approaches a structure requiring a change in direction of the percutaneous device.

In accordance with another embodiment, a method for controlling movement of a percutaneous device includes providing a workstation including a control and a display device, providing an actuating mechanism configured to engage and to impart movement to the percutaneous device, displaying an image on the display device, the image showing a structure being traversed by the percutaneous device, identifying a point on the structure requiring a change in direction of the percutaneous device, identifying a point on the percutaneous device, operating the control to generate a control signal, moving the percutaneous device relative to the structure via the actuating mechanism in response to the control signal, and slowing movement of the percutaneous device via the actuating mechanism as the identified point on the percutaneous device approaches the identified point on the structure.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION OF THE PREFERRED EMBODIMENTS

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
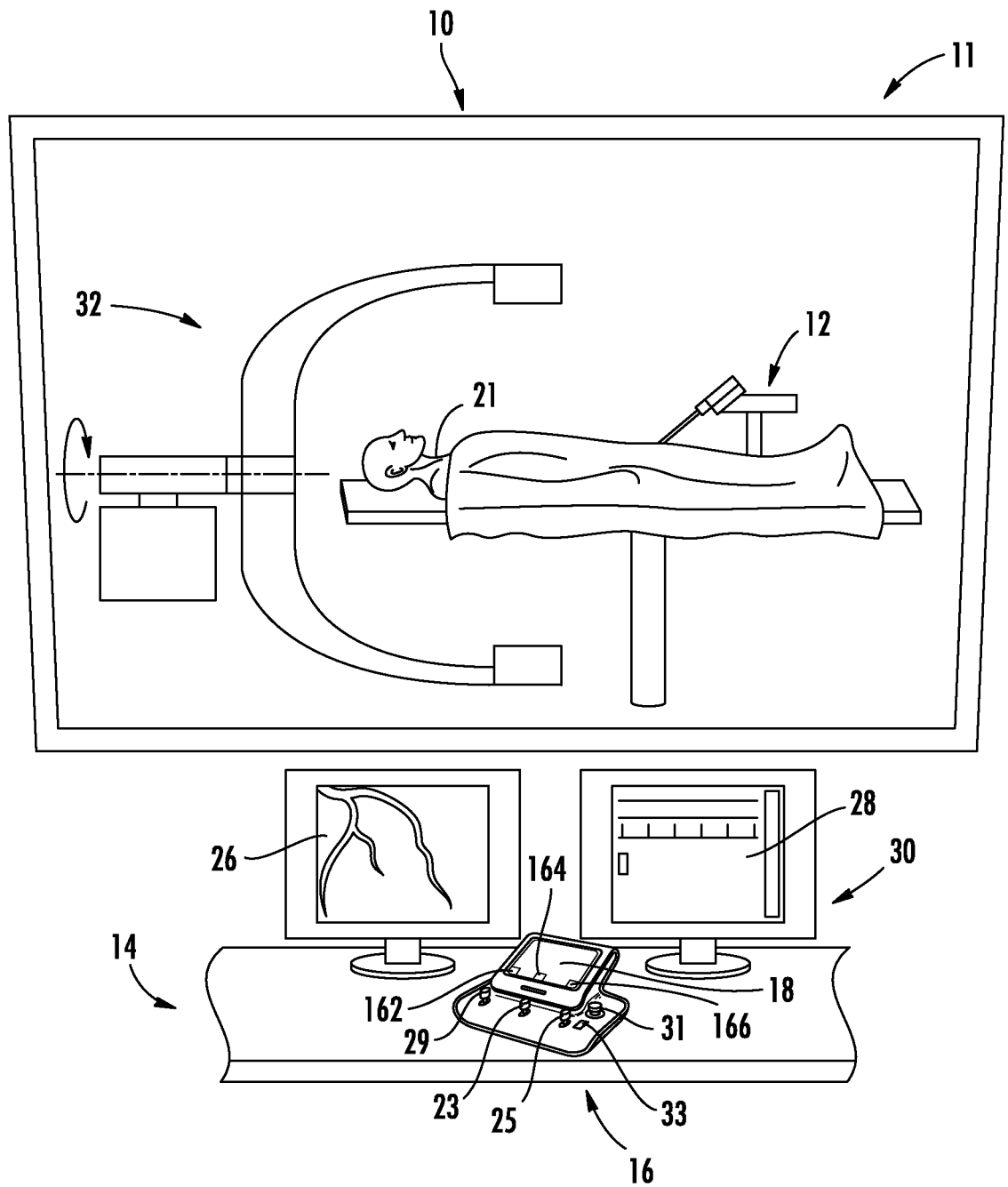
FIG. 1 is a perspective view of a catheter procedure system according to an exemplary embodiment.

Referring to FIG. 1, a catheter procedure system 10 is shown. Catheter procedure system 10 may be used to perform catheter based medical procedures (e.g., percutaneous intervention procedures). Percutaneous intervention procedures may include diagnostic catheterization procedures during which one or more catheters are used to aid in the diagnosis of a patient's disease. For example, during one embodiment of a catheter based diagnostic procedure, a contrast media is injected into one or more coronary arteries through a catheter and an image of the patient's heart is taken. Percutaneous intervention procedures may also include catheter based therapeutic procedures (e.g., balloon angioplasty, stent placement, treatment of peripheral vascular disease, etc.) during which a catheter is used to treat a disease. It should be noted, however, that one skilled in the art would recognize that, certain specific percutaneous intervention devices or components (e.g., type of guide wire, type of catheter, etc.) will be selected based on the type of procedure that is to be performed. Catheter procedure system 10 is capable of performing any number of catheter based medical procedures with minor adjustments to accommodate the specific percutaneous devices to be used in the procedure. In particular, while the embodiments of catheter procedure system 10 described herein are explained primarily in relation to the diagnosis and/or treatment of coronary disease, catheter procedure system 10 may be used to diagnose and/or treat any type of disease or condition amenable to diagnosis and/or treatment via a catheter based procedure.

Catheter procedure system 10 includes lab unit 11 and workstation 14. Catheter procedure system 10 includes a robotic catheter system, shown as bedside system 12, located within lab unit 11 adjacent patient 21. Generally, bedside system 12 may be equipped with the appropriate percutaneous devices (e.g., guide wires, guide catheters, working catheters, catheter balloons, stents, diagnostic catheters, etc.) or other components (e.g., contrast media, medicine, etc.) to allow the user to perform a catheter based medical procedure. A robotic catheter system, such as bedside system 12, may be any system configured to allow a user to perform a catheter-based medical procedure via a robotic system by operating various controls such as the controls located at workstation 14. Bedside system 12 may include any number and/or combination of components to provide bedside system 12 with the functionality described herein. Various embodiments of bedside system 12 are described in detail in P.C.T. International Application No. PCT/US2009/042720, filed May 4, 2009, which is incorporated herein by reference in its entirety.

In one embodiment, bedside system 12 may be equipped to perform a catheter based diagnostic procedure. In this embodiment, bedside system 12 may be equipped with one or more of a variety of catheters for the delivery of contrast media to the coronary arteries. In one embodiment, bedside system 12 may be equipped with a first catheter shaped to deliver contrast media to the coronary arteries on the left side of the heart, a second catheter shaped to deliver contrast media to the coronary arteries on the right side of the heart, and a third catheter shaped to deliver contrast media into the chambers of the heart.

In another embodiment, bedside system 12 may be equipped to perform a catheter based therapeutic procedure. In this embodiment, bedside system 12 may be equipped with a guide catheter, a guide wire, and a working catheter (e.g., a balloon catheter, a stent delivery catheter, ablation catheter, etc.). In one embodiment, bedside system 12 may equipped with a working catheter that includes a secondary lumen that is threaded over the guide wire during a procedure. In another embodiment, bedside system 12 may be equipped with an over-the-wire working catheter that includes a central lumen that is threaded over the guide wire during a procedure. In another embodiment, bedside system 12 may be equipped with an intravascular ultrasound (IVUS) catheter. In another embodiment, any of the percutaneous devices of bedside system 12 may be equipped with positional sensors that indicate the position of the component within the body.

Bedside system 12 is in communication with workstation 14, allowing signals generated by the user inputs and control system of workstation 14 to be transmitted to bedside system 12 to control the various functions of beside system 12. Bedside system 12 also may provide feedback signals (e.g., operating conditions, warning signals, error codes, etc.) to workstation 14. Bedside system 12 may be connected to workstation 14 via a communication link 38 that may be a wireless connection, cable connectors, or any other means capable of allowing communication to occur between workstation 14 and beside system 12.

Workstation 14 includes a user interface 30. User interface 30 includes controls 16. Controls 16 allow the user to control bedside system 12 to perform a catheter based medical procedure. For example, controls 16 may be configured to cause bedside system 12 to perform various tasks using the various percutaneous devices with which bedside system 12 may be equipped (e.g., to advance, retract, or rotate a guide wire, advance, retract, or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure, etc.). In some embodiments, one or more of the percutaneous intervention devices may be steerable, and controls 16 may be configured to allow a user to steer one or more steerable percutaneous device. In one such embodiment, bedside system 12 may be equipped with a steerable guide catheter, and controls 16 may also be configured to allow the user located at remote workstation 14 to control the bending of the distal tip of a steerable guide catheter.

In one embodiment, controls 16 include a touch screen 18, a dedicated guide catheter control 29, a dedicated guide wire control 23, and a dedicated working catheter control 25. In this embodiment, guide wire control 23 is a joystick configured to advance, retract, or rotate a guide wire, working catheter control 25 is a joystick configured to advance, retract, or rotate a working catheter, and guide catheter control 29 is a joystick configured to advance, retract, or rotate a guide catheter. In addition, touch screen 18 may display one or more icons (such as icons 162, 164, and 166) that control movement of one or more percutaneous devices via bedside system 12. Controls 16 may also include a balloon or stent control that is configured to inflate or deflate a balloon and/or a stent. Each of the controls may include one or more buttons, joysticks, touch screens, etc., that may be desirable to control the particular component to which the control is dedicated.

Controls 16 may include an emergency stop button 31 and a multiplier button 33. When emergency stop button 31 is pushed a relay is triggered to cut the power supply to bedside system 12. Multiplier button 33 acts to increase or decrease the speed at which the associated component is moved in response to a manipulation of guide catheter control 29, guide wire control 23, and working catheter control 25. For example, if operation of guide wire control 23 advances the guide wire at a rate of 1 mm/sec, pushing multiplier button 33 may cause operation of guide wire control 23 to advance the guide wire at a rate of 2 mm/sec. Multiplier button 33 may be a toggle allowing the multiplier effect to be toggled on and off. In another embodiment, multiplier button 33 must be held down by the user to increase the speed of a component during operation of controls 16.

User interface 30 may include a first monitor 26 and a second monitor 28. First monitor 26 and second monitor 28 may be configured to display information or patient specific data to the user located at workstation 14. For example, first monitor 26 and second monitor 28 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In one embodiment, monitors 26 and/or 28 may be configured to display an image of a portion of the patient (e.g., the patient's heart) at one or more magnification levels. In addition, first monitor 26 and second monitor 28 may be configured to display procedure specific information (e.g., duration of procedure, catheter or guide wire position, volume of medicine or contrast agent delivered, etc.). Monitor 26 and monitor 28 may be configured to display information regarding the position and/or bend of the distal tip of a steerable guide catheter. Further, monitor 26 and monitor 28 may be configured to display information to provide the functionalities associated with the various modules of controller 40 discussed below. In another embodiment, user interface 30 includes a single screen of sufficient size to display one or more of the display components and/or touch screen components discussed herein.

Catheter procedure system 10 also includes an imaging system 32 located within lab unit 11. Imaging system 32 may be any medical imaging system that may be used in conjunction with a catheter based medical procedure (e.g., non-digital x-ray, digital x-ray, CT, MRI, ultrasound, etc.). In an exemplary embodiment, imaging system 32 is a digital x-ray imaging device that is in communication with workstation 14. As shown in FIG. 1, imaging system 32 may include a C-arm that allows imaging system 32 to partially or completely rotate around patient 21 in order to obtain images at different angular positions relative to patient 21 (e.g., sagittal views, caudal views, cranio-caudal views, etc.).

Imaging system 32 is configured to take x-ray images of the appropriate area of patient 21 during a particular procedure. For example, imaging system 32 may be configured to take one or more x-ray images of the heart to diagnose a heart condition. Imaging system 32 may also be configured to take one or more x-ray images during a catheter based medical procedure (e.g., real-time images) to assist the user of workstation 14 to properly position a guide wire, guide catheter, working catheter, stent, etc. during the procedure. The image or images may be displayed on first monitor 26 and/or second monitor 28.

In addition, the user of workstation 14 may be able to control the angular position of imaging system 32 relative to the patient to obtain and display various views of the patient's heart on first monitor 26 and/or second monitor 28. Displaying different views at different portions of the procedure may aid the user of workstation 14 properly move and position the percutaneous devices within the 3D geometry of the patient's heart. For example, displaying the proper view during a procedure may allow the user to view a patient's vascular system from the proper angle to ensure that the distal tip of a steerable guide catheter is bent in the proper way to ensure the catheter is moved as intended. In an exemplary embodiment, imaging system 32 may be any 3D imaging modality of the past, present, or future, such as an x-ray based computed tomography (CT) imaging device, a magnetic resonance imaging device, a 3D ultrasound imaging device, etc. In this embodiment, the image of the patient's heart that is displayed during a procedure may be a 3D image. In addition, controls 16 may also be configured to allow the user positioned at workstation 14 to control various functions of imaging system 32 (e.g., image capture, magnification, collimation, c-arm positioning, etc.).

Figure 2:
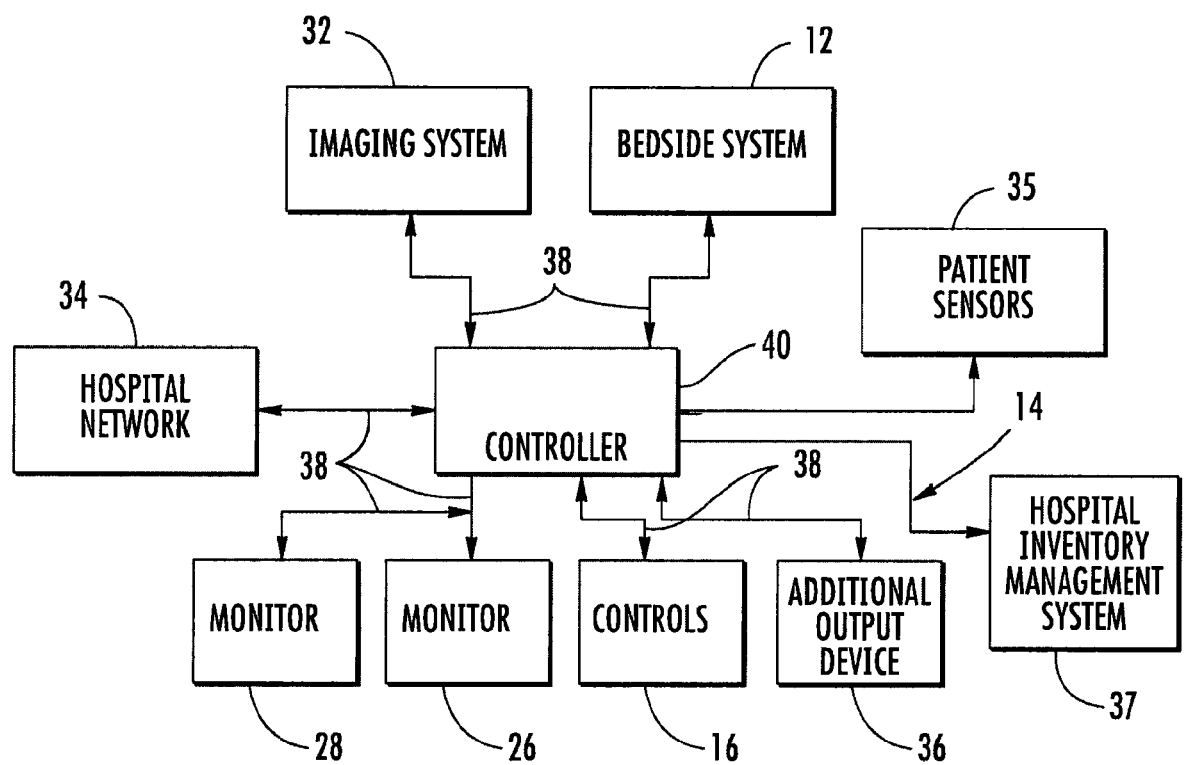
FIG. 2 is a block diagram of a catheter procedure system according to an exemplary embodiment.

Referring to FIG. 2, a block diagram of catheter procedure system 10 is shown according to an exemplary embodiment. Catheter procedure system 10 may include a control system, shown as controller 40. As shown in FIG. 2, controller 40 may be part of workstation 14. Controller 40 is in communication with one or more bedside systems 12, controls 16, monitors 26 and 28, imaging system 32, and patient sensors 35 (e.g., electrocardiogram ("ECG") devices, electroencephalogram ("EEG") devices, blood pressure monitors, temperature monitors, heart rate monitors, respiratory monitors, etc.). In addition, controller 40 may be in communication with a hospital data management system or hospital network 34, one or more additional output devices 36 (e.g., printer, disk drive, cd/dvd writer, etc.), and a hospital inventory management system 37.

Communication between the various components of catheter procedure system 10 may be accomplished via communication links 38. Communication links 38 may be dedicated wires or wireless connections. Communication links 38 may also represent communication over a network. Catheter procedure system 10 may be connected or configured to include any other systems and/or devices not explicitly shown. For example, catheter procedure system 10 may include IVUS systems, image processing engines, data storage and archive systems, automatic balloon and/or stent inflation systems, contrast media and/or medicine injection systems, medicine tracking and/or logging systems, user logs, encryption systems, systems to restrict access or use of catheter procedure system 10, robotic catheter systems of the past, present, or future, etc.

Figure 3:
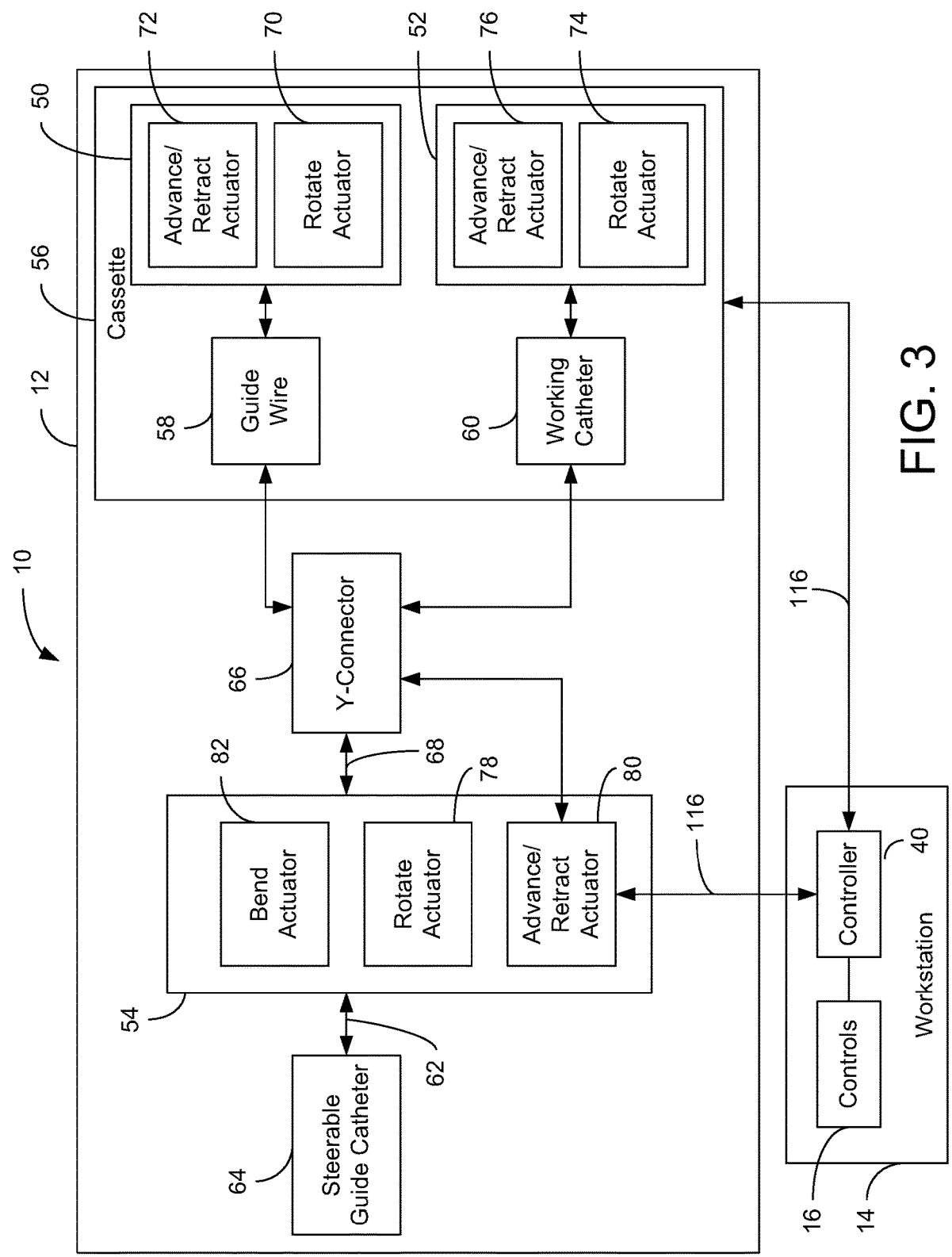
FIG. 3 is a block diagram of a catheter procedure system depicting various actuating mechanisms according to an exemplary embodiment.

Referring to FIG. 3, a block diagram of an embodiment of catheter procedure system 10 is shown according to an exemplary embodiment. Catheter procedure system 10 may include various actuating mechanisms that move an associated percutaneous device in response to a user's manipulation of controls 16. In the embodiment shown, catheter procedure system 10 includes a guide wire actuating mechanism 50, a working catheter actuating mechanism 52, and a guide catheter actuating mechanism 54. In other embodiments, catheter procedure system 10 may include an actuating mechanism for inflating an angioplasty or stent delivery balloon and an actuating mechanism for delivering contrast agent. In the embodiment shown, guide wire actuating mechanism 50 and working catheter actuating mechanism 52 are incorporated within cassette 56. Additional embodiments of bedside system 12 and cassette 56 are described in detail in P.C.T. International Application No. PCT/US2009/042720, filed May 4, 2009, which is incorporated herein by reference in its entirety.

Guide wire actuating mechanism 50 is coupled to guide wire 58 such that guide wire actuating mechanism 50 is able to cause guide wire 58 to advance, retract, and rotate. Working catheter actuating mechanism 52 is coupled to working catheter 60 such that working catheter actuating mechanism 52 is able to cause working catheter 60 to advance, retract, and rotate. Connector 62 couples guide catheter 64 to guide catheter actuating mechanism 54 such that guide catheter actuating mechanism 54 is able to cause guide catheter 64 to advance, retract, and rotate. In various embodiments, guide wire actuating mechanism 50, working catheter actuating mechanism 52, and guide catheter actuating mechanism may each include an engagement structure suitable for engaging the respective percutaneous device such that the actuating mechanism is able to impart axial and/or rotational movement to the percutaneous device.

In one embodiment, cassette 56 is configured to be coupled to a motor drive base. In this embodiment, each of the actuators 70, 72, 74, and 76 of cassette 56 are configured to engage capstans extending from the motor drive base. Motors located within the motor drive base drive (e.g., rotate) the capstans which in turn drive the actuators 70, 72, 74, and 76 of cassette 56. When the actuators 70, 72, 74, and 76 of cassette 56 are engaged with guide wire 58 and working catheter 60, respectively, the actuators 70, 72, 74, and 76 of cassette 56 transfer the rotational movement of the capstans to cause the movement of guide wire 58 and working catheter 60. In another embodiment, the motors that drive the capstans of the motor drive base may be located outside of the base connected to cassette 56 via an appropriate transmission device (e.g., shaft, cable, etc.). In yet another embodiment, cassette 56 includes motors located within cassette 56 associated with the actuators 70, 72, 74, and 76, and cassette 56 is mounted to a base providing a power supply (e.g., battery, AC building power supply, etc.) to the motors within cassette 56.

A Y-connector 66 is coupled to guide catheter actuating mechanism 54 via connector 68. In various embodiments, connector 68 may be a component separate from both Y-connector 66 and guide catheter actuating mechanism 54. In other embodiments, connector 68 may be part of (e.g., integral with) Y-connector 66 or part of actuating mechanism 54. In the embodiment shown, Y-connector 66 is also connected to cassette 56.

In one embodiment, Y-connector 66 includes a first leg, a second leg, and a third leg. The first leg of the Y-connector is connected to or in communication with the internal lumen of guide catheter 64. The second leg is angled away from the longitudinal axis of guide catheter 64. The second leg provides a port for the injection of fluids (e.g., contrast media, medicine, etc.) into the lumen of guide catheter 64. The third leg of Y-connector 66 is coupled to a cassette 56 and receives both guide wire 58 and working catheter 60. Thus, by this arrangement, guide wire 58 and working catheter 60 are inserted through Y-connector 66 into the internal lumen of guide catheter 64.

Guide wire actuating mechanism 50 includes a rotate actuator 70 and an advance/retract actuator 72. Rotate actuator 70 is configured to cause rotation of guide wire 58 about its longitudinal axis. Advance/retract actuator 72 is configured to advance and/or retract guide wire 58 (i.e., to advance and/or retract along the longitudinal axis of the guide wire) within patient 21. Working catheter actuating mechanism 52 includes a rotate actuator 74 and an advance/retract actuator 76. Rotate actuator 74 is configured to cause rotation of working catheter 60 about its longitudinal axis. Advance/retract actuator 76 is configured to advance and/or retract working catheter 60 (i.e., to advance and/or retract along the longitudinal axis of the working catheter) within patient 21. Guide catheter actuating mechanism 54 includes a rotate actuator 78, an advance/retract actuator 80, and a bend actuator 82. Rotate actuator 78 is configured to cause rotation of guide catheter 64 about its longitudinal axis. Advance/retract actuator 80 is configured to advance and/or retract guide catheter 64 (i.e., to advance and/or retract along the longitudinal axis of the guide catheter) within patient 21. In some embodiments, guide catheter 64 may include one or more bend control elements that allow the user to cause bending of the distal tip of guide catheter 64. In such an embodiment, bend actuator 82 causes the distal tip of guide catheter 64 to bend in response to a user's manipulation of controls 16.

As shown in the block diagram of FIG. 3, controls 16 and controller 40 located at workstation 14 are communicably coupled to various portions of bedside system 12 to allow the user to control movement of guide wire 58, working catheter 60 and guide catheter 64 and any other percutaneous devices that bedside system 12 is equipped with. In the embodiment shown, controls 16 and controller 40 are coupled to guide catheter actuating mechanism 54 to allow the user to move guide catheter 64. In addition, controls 16 are coupled to cassette 56 to allow the user to control guide wire 58 via guide wire actuating mechanism 50 and to control working catheter 60 via working catheter actuating mechanism 52.

Figure 4:
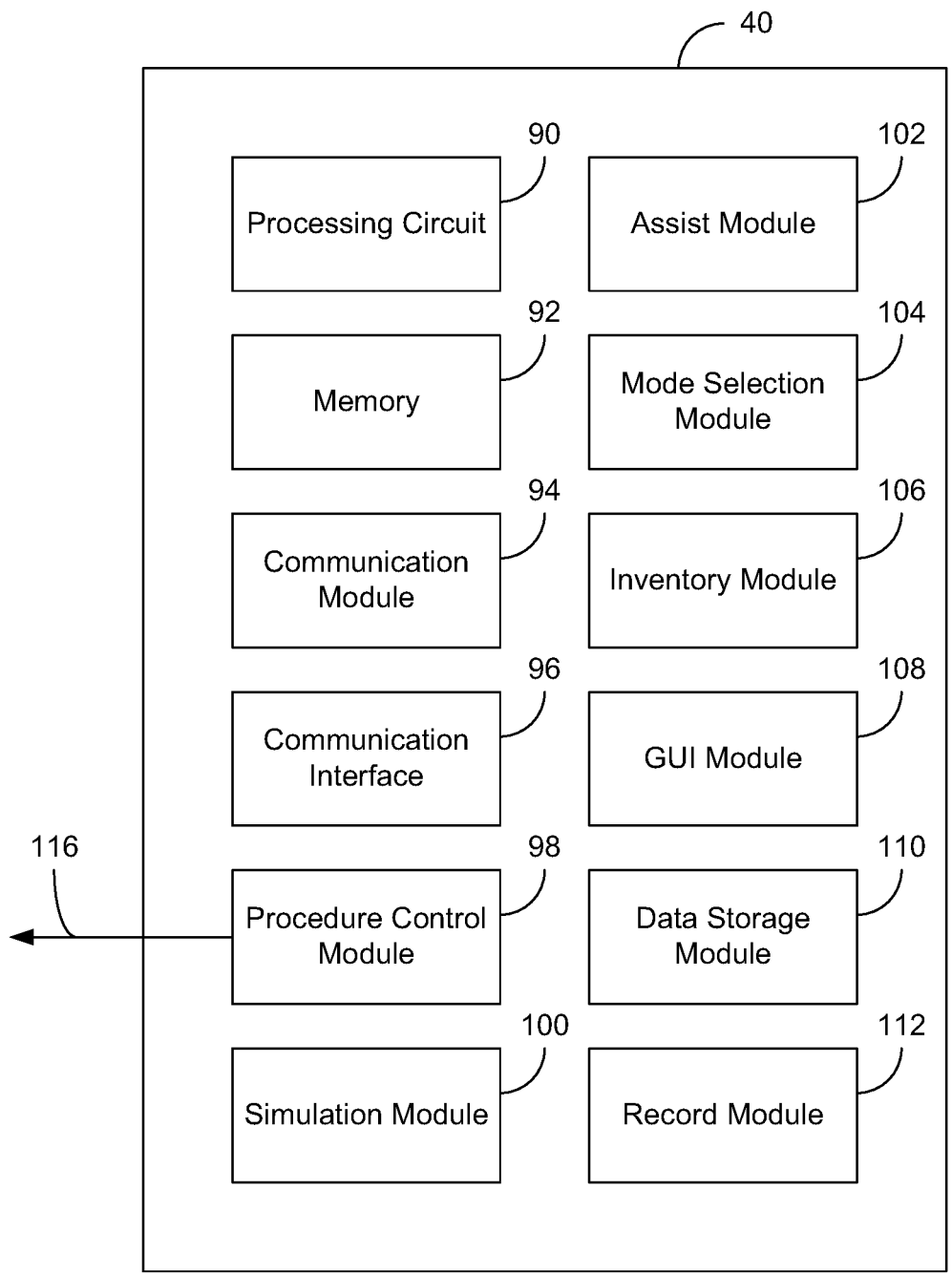
FIG. 4 is a block diagram of a controller for controlling a robotic catheter system according to an exemplary embodiment.

Referring to FIG. 4, a block diagram of controller 40 is shown according to an exemplary embodiment. Controller 40 may generally be an electronic control unit suitable to provide catheter procedure system 10 with the various functionalities described herein. For example, controller 40 may be an embedded system, a dedicated circuit, a general purpose system programmed with the functionality described herein, etc. Controller 40 includes a processing circuit 90, memory 92, communication module or subsystem 94, communication interface 96, procedure control module or subsystem 98, simulation module or subsystem 100, assist control module or subsystem 102, mode selection module or subsystem 104, inventory module or subsystem 106, GUI module or subsystem 108, data storage module or subsystem 110, and record module or subsystem 112.

Processing circuit 90 may be a general purpose processor, an application specific processor (ASIC), a circuit containing one or more processing components, a group of distributed processing components, a group of distributed computers configured for processing, etc., configured provide the functionality of module or subsystem components 94, 98-112. Memory 92 (e.g., memory unit, memory device, storage device, etc.) may be one or more devices for storing data and/or computer code for completing and/or facilitating the various processes described in the present disclosure. Memory 92 may include volatile memory and/or non-volatile memory. Memory 92 may include database components, object code components, script components, and/or any other type of information structure for supporting the various activities described in the present disclosure.

According to an exemplary embodiment, any distributed and/or local memory device of the past, present, or future may be utilized with the systems and methods of this disclosure. According to an exemplary embodiment, memory 92 is communicably connected to processing circuit 90 and module components 94, 98-112 (e.g., via a circuit or any other wired, wireless, or network connection) and includes computer code for executing one or more processes described herein. A single memory unit may include a variety of individual memory devices, chips, disks, and/or other storage structures or systems.

Module or subsystem components 94, 98-112 may be computer code (e.g., object code, program code, compiled code, script code, executable code, or any combination thereof), hardware, software, or any combination thereof, for conducting each module's respective functions. Module components 94, 98-112 may be stored in memory 92, or in one or more local, distributed, and/or remote memory units configured to be in communication with processing circuit 90 or another suitable processing system.

Communication interface 96 includes one or more component for communicably coupling controller 40 to the other components of catheter procedure system 10 via communication links 38. Communication interface 96 may include one or more jacks or other hardware for physically coupling communication links 38 to controller 40, an analog to digital converter, a digital to analog converter, signal processing circuitry, and/or other suitable components. Communication interface 96 may include hardware configured to connect controller 40 with the other components of catheter procedure system 10 via wireless connections. Communication module 94 is configured to support the communication activities of controller 40 (e.g., negotiating connections, communication via standard or proprietary protocols, etc.).

Data storage module 110 is configured to support the storage and retrieval of information by controller 40. In one embodiment, data storage module 110 is a database for storing patient specific data, including image data. In another embodiment, data storage module 110 may be located on hospital network 34. Data storage module 110 and/or communication module 94 may also be configured to import and/or export patient specific data from hospital network 34 for use by controller 40.

Controller 40 also includes a procedure control module 98 configured to support the control of bedside system 12 during a catheter based medical procedure. Procedure control module 98 allows the user to operate bedside system 12 by manipulating controls 16. In various embodiments, procedure control module 98 is configured to generate one or more control signals 116 based upon the user's manipulation of controls 16 and/or other data available to procedure control module 98. As shown in FIG. 3, control signals 116 generated by procedure control module 98 are communicated from controller 40 to the various actuators of bedside system 12. In response to control signals 116, the actuators of cassette 56 cause movement of the guide wire, working catheter and/or guide catheter. Procedure control module 98 may also cause data appropriate for a particular procedure to be displayed on monitors 26 and 28. Procedure control module 98 may also cause various icons (e.g., icons 162, 164, 166, etc.) to be displayed on touch screen 18 that the user may interact with to control the use of bedside system 12.

In one embodiment, procedure control module 98 is configured to cause bedside system 12 to move (e.g., advance, retract, rotate, etc.) the percutaneous devices at a set rate in response to a particular input received by controls 16. For example, procedure control module 98 may be configured such that when guide wire control 23 is actuated, bedside system 12 causes the guide wire to advance, retract or rotate at a set rate. In one embodiment, procedure control module 98 may be configured to allow the user to control the rate of movement of a device based on the user's interaction with controls 16. In one embodiment, the movement rate of a percutaneous device caused by bedside system 12 is proportional to the amount of displacement of the control. For example, where controls 23, 25 and 29 are joystick controls, the movement rate of a percutaneous device caused by bedside system 12 is a function of or is proportional to the degree of displacement of the joystick from the resting position.

As noted above, controller 40 includes a GUI module 108 the controls the display of various information on the display devices (e.g., monitors 26 and 28, touch screen 18, etc.) of workstation 14. In one embodiment, GUI module 108 is configured to display image data captured by imaging system 32 during a procedure to assist the user of catheter procedure system 10 perform a procedure. In one exemplary embodiment, shown in FIGS. 5 and 6, GUI module 108 is configured to cause the display of an image of a portion of the patient, shown for example as patient's heart 120 in FIG. 5 or coronary arteries 126 in FIG. 6, during a cardiac catheterization procedure on a monitor or display device, such as monitor 26.

Figure 5:
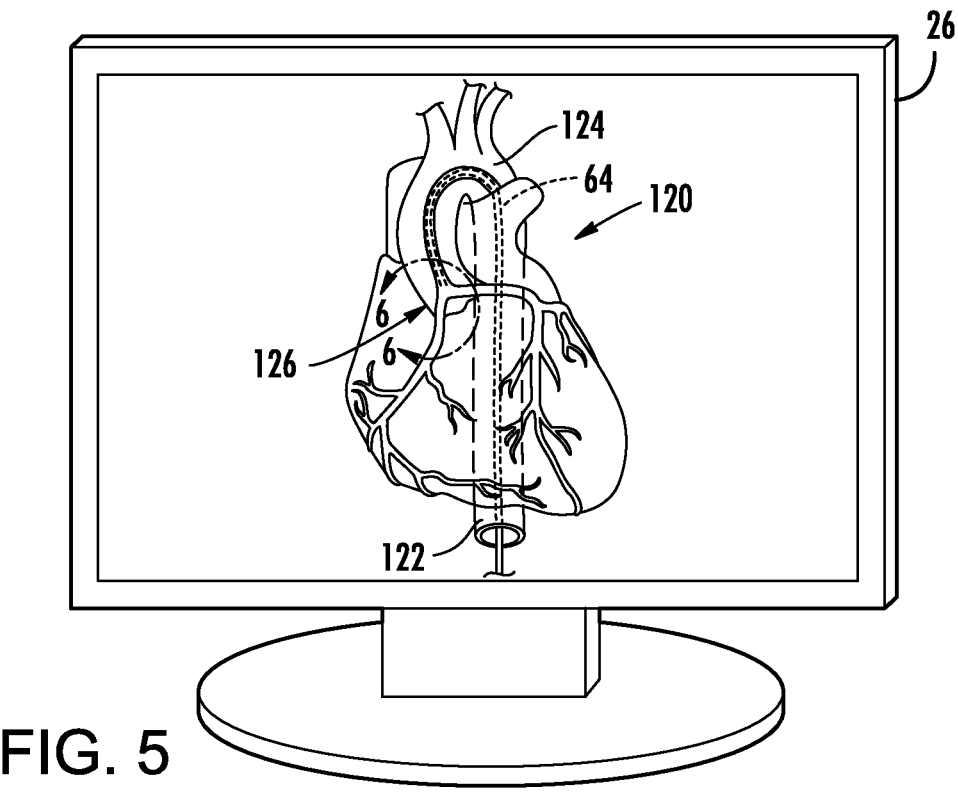
FIG. 5 is a display monitor showing a patient's heart during a procedure at a low level of magnification according to an exemplary embodiment.
Figure 6:
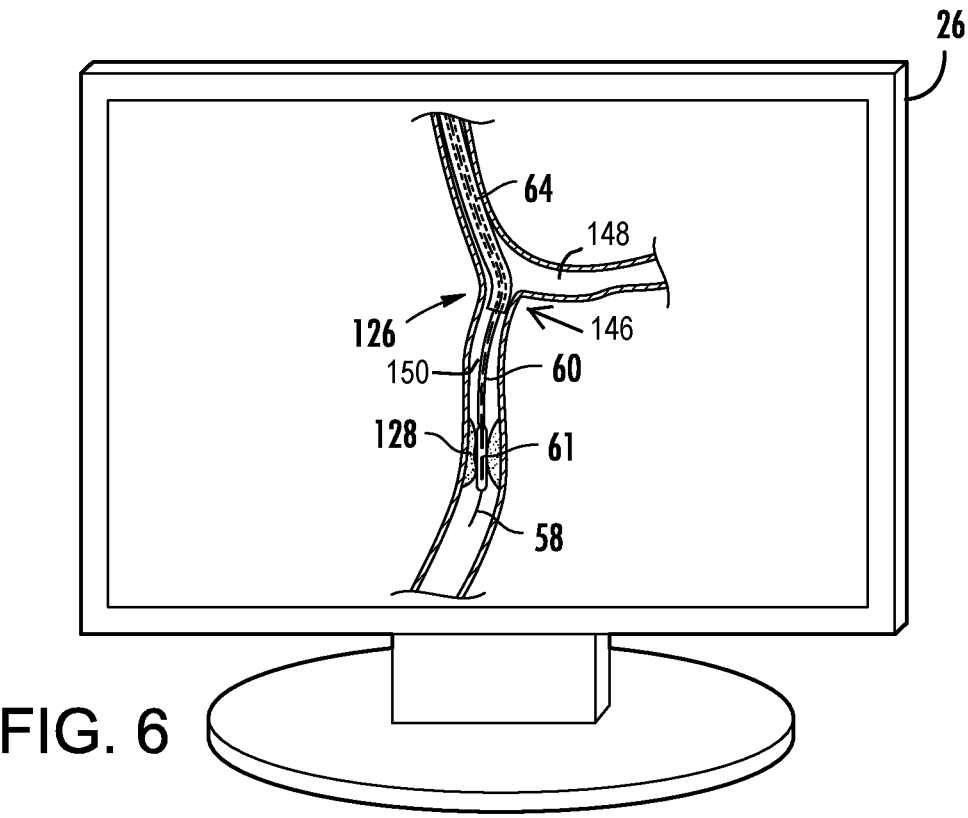
FIG. 6 is a display monitor showing a magnified portion of a patient's heart during a procedure according to an exemplary embodiment.

Referring to FIGS. 5 and 6, an exemplary balloon angioplasty therapeutic procedure is shown. During the exemplary procedure shown, an incision is made, usually in the groin. A guide catheter 64 is inserted through the incision into the femoral artery. Bedside system 12 is operated via controls 16 and controller 40 to feed guide catheter 64 through the patient's aorta 122 over the aortic arch 124 until guide catheter 64 is positioned near either the left or right ostium leading into the patient's coronary arteries 126. Bedside system 12 is then operated via controls 16 and controller 40 to feed guide wire 58 through guide catheter 64 until guide wire 58 extends across lesion 128. Next, bedside system 12 is operated via controls 16 and controller 40 to advance working catheter 60 over guide wire 58 to position balloon 61 across lesion 128. Once working catheter 60 and balloon 61 is in place, balloon 61 is inflated to compress lesion 128 and to stretch the artery open thereby increasing blood flow to the heart. Balloon 61 is then deflated, guide wire 58, working catheter 60 and guide catheter 64 are removed, and the incision is closed. Coronary arteries 126 includes a fork 146 having a first branch 148 and a second branch 150.

In one embodiment, GUI module 108 may be configured to allow the user to alter the magnification or zoom level of an image displayed on monitor 26 during a procedure. As shown in FIG. 5, an image (e.g., an x-ray fluoroscope image) of a patient's heart 120 is displayed on monitor 26 having a first, relatively low magnification or zoom level. In another embodiment, the first magnification level might be an unmagnified level. During a procedure, the user may choose to view an image of heart 120 at the first, relatively low magnification level while the user moves the percutaneous devices through the larger vessels (e.g., aorta 122, aortic arch 124, etc.) of a patient's vascular system.

As shown in FIG. 6, an image of heart 120 may also be displayed on monitor 26 at a second, relatively high magnification or zoom level. During a procedure, the user may choose to view an image of heart 120 at the second, relatively high magnification level while the user performs fine or precise movements of the percutaneous devices. For example, as shown in FIG. 6 the user may choose to zoom in on the coronary arteries 126 when the user is moving guide wire 58 and working catheter 60 to treat lesion 128. Further a higher magnification level may also be appropriate when the percutaneous devices are being moved through bends in the vascular system or through portions of the vascular system susceptible to damage. It should be understood that, while FIGS. 5 and 6, display only two different magnification or zoom levels, GUI module 108 may be configured to display images from imaging system 32 at a plurality of zoom levels between a maximum magnification level and a minimum magnification level.

Workstation 14 may be configured to allow the user to select or change magnification levels in a variety of ways. For example, in one embodiment, GUI module 108 may be configured to display an icon on touch screen 18 representing the patient's heart. By touching portions of the icon representing the patient's heart on touch screen 18, the user may alter the magnification level of image of heart 120 displayed on monitor 26. For example, the user may touch the coronary artery portion of the heart icon to display a magnified image of the coronary arteries 126 of heart 120, as shown in FIG. 6. In another embodiment, the magnification level may be changed by selecting an area of heart 120 on the display of FIG. 5. The selection of the area to be magnified may be accomplished by selecting the area with a pointing device, like a mouse. In another embodiment, the magnification level may be set by a dial, drop-down menu, etc.

In another embodiment, one of the modules (e.g., GUI module 108) of controller 40 may be configured to automatically adjust or select the magnification level. In this embodiment, the location of the tip of the device currently being moved may be automatically determined by controller 40. For example, the tip of the device may be determined by image processing of image data received from imaging system 32, from positional sensors associated with the percutaneous device, etc. In one embodiment, the magnification level may increase as the tip of the percutaneous device approaches the coronary arteries or the lesion to be treated.

In an exemplary embodiment, procedure control module 98 may be configured to control the movement of the percutaneous device based upon the magnification level of the image displayed on monitor 26. In various embodiments, control signals 116 generated by controller 40 may be based on both the magnification level of the image displayed on monitor 26 and based upon the user's manipulation of controls 16. In one embodiment, procedure control module 98 is configured such that the speed and/or acceleration of advancement, retraction or rotation caused by the actuators of bedside system 12 in response to control signals 116 is a function of the magnification level of the image displayed on monitor 26. In one embodiment, procedure control module 98 is configured such that the speed and/or acceleration of advancement, retraction or rotation caused by the actuators of bedside system 12 in response to control signals 116 may be inversely related (e.g., inversely proportional) to the magnification level of the image displayed on monitor 26.

In one embodiment, the speed of advancement or retraction of the percutaneous device in response to a user's manipulation of controls 16 is a function (e.g., linear function, non-linear function, step-function, etc.) of the magnification level of the image displayed on monitor 26. In one such embodiment, the speed of advancement or retraction of the percutaneous device in response to a user's manipulation of controls 16 is inversely related to the magnification level of the image displayed on monitor 26. For example, in an embodiment where controls 23, 25 and 29 are joystick controls, the movement rate of a percutaneous device caused by bedside system 12 is proportional to the degree of displacement of the joystick from the resting position and is inversely related to the magnification level. Thus, in this embodiment, when the image displayed on monitor 26 is at the magnification level shown in FIG. 5 (i.e., a lower magnification level), guide wire 58, working catheter 60 and/or guide catheter 64 will be moved at a relatively higher speed in response to a particular displacement of the joystick controls 23, 25, and 29 than when the image displayed on monitor 26 is at the magnification level shown in FIG. 6. In this embodiment, procedure control module 98 is configured to generate a first control signal 116 based on the particular displacement of controls 23, 25 and/or 29 and based upon the magnification level of the image displayed in FIG. 5 and to generate a second control signal 116 based on the particular displacement of controls 23, 25 and/or 29 and based upon the magnification level of the image displayed in FIG. 6. In this embodiment, the movement (e.g., the speed, acceleration, etc.) of the percutaneous device (e.g., guide wire, working catheter, guide catheter, etc.) caused by the actuators of bedside system 12 in response to the first control signal will be greater than the movement (e.g., the speed, acceleration, etc.) of the percutaneous device (e.g., guide wire, working catheter, guide catheter, etc.) caused by the actuators of bedside system 12 in response to the second control signal. In various embodiments, the advance, retract and/or rotation speeds/accelerations of the percutaneous devices may be based upon the magnification level.

Controlling the movement of the percutaneous device based on the magnification level of the image displayed on the monitor may provide for improved control over movement of the percutaneous device. For example, during a procedure, the user of catheter procedure system 10 watches the progress of the tip of the moving percutaneous device in the image displayed on monitor 26 to help the user navigate the device through the patient's blood vessels. By slowing the speed of advancement or retraction as magnification of the image increases, the user of catheter procedure system 10 will be better able to ensure that the tip of the device stays visible in the image displayed on monitor 26 because the likelihood that the tip of the percutaneous device will quickly or unexpectedly move outside the frame of the displayed image will be decreased by the lower rate of speed. Further, slowing the speed and/or acceleration of the percutaneous device based on the magnification level may also provide for more precise navigation of the device because the magnification increases and the corresponding speed and acceleration decrease will typically occur when the percutaneous device is being moved within the smaller blood vessels.

In various exemplary embodiments, procedure control module 98 may be configured to generate a control signal 116 to control the movement of the percutaneous device based upon the position of the percutaneous device relative to a particular structure or region of the patient's vascular system and/or based upon a size of a particular structure or region of the patient's vascular system. In one such embodiment, procedure control module 98 is configured such that the speed of advancement or retraction of the percutaneous device in response to a user's manipulation of controls 16 is a function (e.g., linear function, non-linear function, step-function, etc.) of the proximity of a percutaneous device to a lesion (e.g., lesion 128). In one exemplary embodiment, the speed of advancement or retraction of the percutaneous device in response to a user's manipulation of controls 16 is directly related to the distance between a lesion and the tip of a percutaneous device. For example, in an embodiment where controls 23, 25 and 29 are joystick controls, the movement rate of a percutaneous device caused by bedside system 12 is proportional to the degree of displacement of the joystick from the resting position and is directly related to the distance between a lesion and the tip of a percutaneous device. Thus, in this embodiment, the speed of the percutaneous device may be decreased as the tip of the percutaneous device approaches the lesion. In one embodiment, the location of the lesion and of the tip of the percutaneous device may be automatically determined by image processing of image data captured from imaging system 32. In another embodiment, the location of the lesion and of the tip of the percutaneous device may be manual identified by the user by selecting the lesion and the tip of the percutaneous device using an input device such as touch screen 18.

In another embodiment, procedure control module 98 is configured to generate a control signal 116 to control percutaneous device movement such that the speed of advancement or retraction of the percutaneous device in response to a user's manipulation of controls 16 is a function (e.g., linear function, non-linear function, step-function, etc.) of the size of the lumen of the blood vessel that the tip of the percutaneous device is currently traversing. In one exemplary embodiment, the speed of advancement or retraction of the percutaneous device in response to a user's manipulation of controls 16 is directly related to the size of the lumen of the blood vessel that the tip of the percutaneous device is currently traversing. For example, in an embodiment where controls 23, 25 and 29 are joystick controls, the movement rate of a percutaneous device caused by bedside system 12 is proportional to the degree of displacement of the joystick from the resting position and is directly related to the size of the lumen of the blood vessel that the tip of the percutaneous device is currently traversing. Thus, in this embodiment, the percutaneous device may move at a slower speed when traversing the coronary arteries than when traversing the aorta, and the percutaneous device may move at a slower speed when traversing a partially occluded coronary artery than when traversing an non-occluded coronary artery. In various embodiments, different indications of lumen size (e.g., diameter of the lumen, radius of the lumen, circumference of the lumen, cross-sectional area of the lumen, etc.) may be used by procedure control module 98 in controlling the speed of the percutaneous device. In one embodiment, the lumen size may be automatically determined by image processing of image data captured from imaging system 32. In another embodiment, the lumen size may be manually identified by the user by selecting or highlighting a portion of lumen using an input device such as touch screen 18. For example, in one embodiment, the user may trace the border of the lumen of a blood vessel displayed on touch screen 18 to determine lumen circumference and/or cross-sectional area.

In another embodiment, procedure control module 98 may be configured to aid in the alignment of a treatment device, such as an inflatable treatment device (e.g., a stent or angioplasty balloon), relative to a lesion to be treated. For example, in one embodiment, procedure control module 98 may be configured to generate control signals 116 to slow and eventually stop the movement of working catheter 60 as balloon 61 (or a stent) approaches the end of lesion 128. In one such embodiment, the user may identify or select a point located on lesion 128 and a point located on balloon 61 using an input device such as touch screen 18. As the identified point located on balloon 61 approaches the identified point on the lesion, controller 40 automatically alters control signal 116 such that the speed of working catheter 60 is decreased. In addition, controller 40 may be configured to automatically cease generation of control signal 116 such that advancement of working catheter 60 is stopped when the selected point on the lesion aligns with the selected point on balloon 61. In one exemplary embodiment, procedure control module 98 is configured to reduce the speed of working catheter 60 when the tip of the working catheter is about 10 to 20 mm from the selected point on the lesion. Thus, in this embodiment, control signals 116 generated by controller 40 are based upon the user's manipulation of controls 16 and the relative positioning of the identified point on lesion 128 to a point located on balloon 61. In one embodiment, procedure control module 98 is configured to allow the user to select and/or toggle on and off the alignment assistance function via controls 16. By automatically slowing movement of the percutaneous device as the target positioned is approached, controller 40 may aid in the precise positioning of the percutaneous device.

In one exemplary, the identified point on lesion 128 is the mid-point of the lesion and the point located on balloon 61 is the mid-point of balloon 61. In another exemplary embodiment, the identified point on lesion 128 is the distal end of the lesion and the point located on balloon 61 is the distal end of balloon 61. In one embodiment, the relative positioning of the identified point on lesion 128 to the point located on balloon 61 is determined by image processing image data received from imaging system 32. In another embodiment, the relative positioning of the identified point on lesion 128 to the point located on balloon 61 is determined by location sensors associated with balloon 61.

In another embodiment, procedure control module 98 may be configured to aid in controlling movement of the percutaneous device through the patient's vascular system by automatically slowing the axial movement of the percutaneous device as the tip of the percutaneous device approaches an area requiring a change in direction of the percutaneous device (e.g., a bend, fork, turn, etc. in the patient's vascular system). Such slowing prior to the bend or fork may facilitate the user's ability to guide or steer the percutaneous device through the bend or fork. In this embodiment, the control signal 116 is based upon the user's manipulation of an input device or control and based upon the proximity of the distal tip of the percutaneous device to an upcoming structure that requires a change in direction to navigate. Thus, procedure control module 98 automatically generates the control signal to slow the percutaneous device as the percutaneous device approaches the turn without requiring the user to manually operate the control to plan for the upcoming change in direction.

Figure 7:
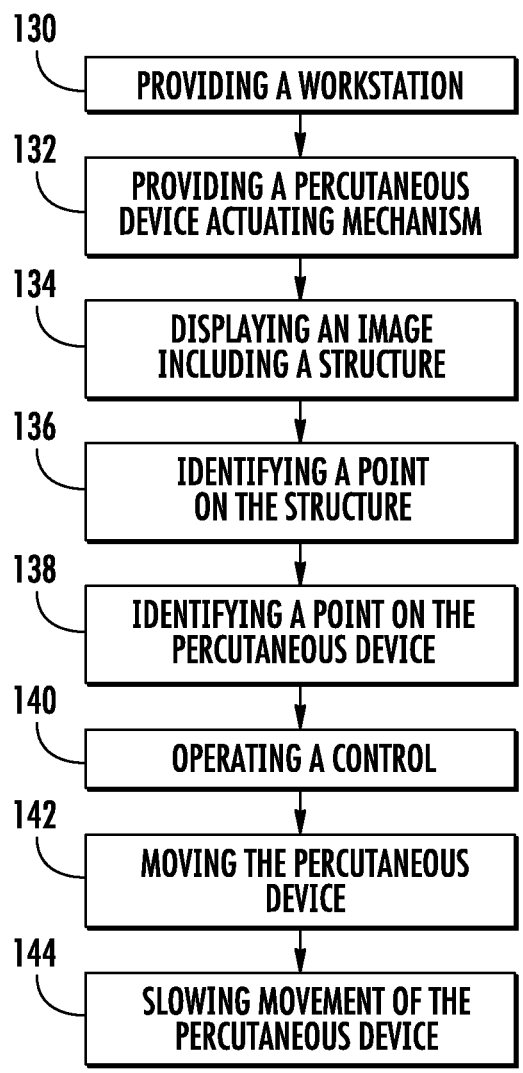
FIG. 7 is a flow diagram showing control of a percutaneous device within a patient according to an exemplary embodiment.

FIG. 7 shows a flow diagram of a method of controlling movement of a percutaneous device within a patient according to an exemplary embodiment. At step 130, a workstation including a control and a display device is provided, and at step 132 an actuating mechanism configured to engage and to impart movement to the percutaneous device is provided. At step 134, an image of a portion of the patient (e.g., heart, coronary arteries, etc.) is displayed on the display device, and the image shows a structure to be navigated by the percutaneous device. For example, the structure may be a structure in need of treatment using the percutaneous device (e.g., a plaque, atherosclerosis, lesion, defective or diseased heart valve, etc.). At step 136, a point on the structure is identified, and at step 138, a point on the percutaneous device is identified. At step 140, the control is operated to generate a control signal, and at step 142, the percutaneous device is moved relative to the structure via the actuating mechanism in response to the control signal. At step 144, the movement of the percutaneous device is slowed via the actuating mechanism as the identified point of the percutaneous device approaches the identified point of the structure. In one embodiment, at step 144, the actuating mechanism is automatically controlled by controller 40 automatically generating control signals 116 to slow the percutaneous device as discussed above. In various alternative embodiments, in combination with one or more of the above identified steps, the method may also include generating the control signals based on the magnification level of the displayed image as discussed above relative to FIGS. 5 and 6. In another embodiment, the structure may be a bend, turn or fork in the patient's vasculature and the identified point on the percutaneous device may be the tip of the percutaneous device.

Further modifications and alternative embodiments of various aspects of the invention will be apparent to those skilled in the art in view of this description. Accordingly, this description is to be construed as illustrative only. The construction and arrangements as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A method for controlling movement of a first percutaneous device comprising:
generating a control signal based at least partly on a user input via a control, the user input indicating a guiding or steering of the first percutaneous device;
moving the first percutaneous device relative to a structure being traversed by the first percutaneous device via an actuating mechanism configured to engage and to impart movement to the first percutaneous device, in response to the control signal; and
slowing movement of the first percutaneous device via the actuating mechanism as an identified point on the first percutaneous device approaches an identified point on the structure, wherein the control signal causes the actuating mechanism to slow movement by changing speed of the first percutaneous device based on the guiding the first percutaneous device indicated by the user input and as a function of a distance to the structure, the function being at least one of a linear function, a non-linear function or a step function,
wherein the first percutaneous device is configured to guide a second percutaneous device to a desired position in a vasculature, wherein the second device is at least one of a guide wire, a guide catheter or a working catheter,
wherein the movement of the first percutaneous device is controlled by actuators provided in the actuating mechanism, the actuators being provided at a proximal portion of the first percutaneous device, wherein the speed of the first percutaneous device is a function of a magnification level of an image displayed on a display device.

2. The method according to claim 1, wherein the identified point on the structure is a fork in a patient's vasculature.

3. A method for controlling movement of a percutaneous device comprising:
selecting a magnification level of an image displayed on a display device from at least a first magnification level and a second magnification level, wherein the first magnification level is less than the second magnification level;
providing a control system to generate a control signal based on a user input at a workstation and the magnification level; and
moving the percutaneous device relative to a structure being traversed by the precutaneous device via an actuating mechanism configured to engage and to impart movement to the percutaneous device in response to the control signal,
wherein the input device is a joystick,
wherein moving the percutaneous device includes moving the percutaneous device at a speed that is a function of a displacement of the joystick and the magnification level, and
wherein the image shows the structure being traversed by the percutaneous device.

4. The method according to claim 3, wherein moving the percutaneous device includes moving the percutaneous device at a speed inversely proportional to the magnification level.

5. The method according to claim 3, wherein moving the percutaneous device includes moving the percutaneous device at a speed that is one of a linear function of the magnification level and a nonlinear function of the magnification level.

6. The method according to claim 3, wherein moving the percutaneous device includes moving the percutaneous device at a speed that is a step level of the magnification level.

7. The method according to claim 3, wherein an acceleration of the percutaneous device is caused by the actuating mechanism in response to the control signal changes based on the magnification level of the image.

8. The method according to claim 3, wherein selecting the magnification level is automatically selected by the control system based on a location of a tip of the percutaneous device within the structure.

9. The method according to claim 8, wherein the control system automatically increases the magnification level as the tip of the percutaneous device within approaches a lesion to be treated.

10. A method for controlling movement of a percutaneous device comprising:
automatically selecting a magnification level of an image display on a display device from at least a first magnification level and a second magnification level, wherein the first magnification level is less than the second magnification level;
generating a control signal based on a user input to a workstation; and
moving the percutaneous device relative to a structure being traversed by the percutaneous device via an actuating mechanism, configured to engage and to impart movement to the percutaneous device, in response to the control signal,
wherein moving the percutaneous device includes moving the percutaneous device at a speed as a function of the magnification level, and
wherein the structure being traversed by the percutaneous device is displayed in the image.

11. The method according to claim 10, wherein automatically selecting the magnification level is based on a location of a tip of the percutaneous device within the structure.

12. The method according to claim 11, wherein the display device is configured to display an image captured by an imaging system positioned outside of a vasculature, the imaging system determining a location of the percutaneous device by image processing of the image.

13. The method according to claim 12, the magnification level is automatically adjusted as the tip of the percutaneous devices moves within the structure.

14. The method according to claim 13, wherein the magnification level automatically increases as the tip of the percutaneous device approaches a lesion to be treated.

* * * * *